(12) United States Patent
Vienney et al.

(10) Patent No.: US 10,405,899 B2
(45) Date of Patent: Sep. 10, 2019

(54) DEVICES, METHODS AND SYSTEMS FOR REMEDYING OR PREVENTING FRACTURES

(75) Inventors: Cécile Vienney, Belin Beliet (FR); Stéphane Corp, Paris (FR); Marek Szpalski, Brussels (BE); Robert Gunzburg, Berchem (BE); Max Aebi, Bienne (CH)

(73) Assignee: Hyprevention SAS, Pessac (FR)

( * ) Notice: Subject to any disclaimer, the term of this patent is extended or adjusted under 35 U.S.C. 154(b) by 6 days.

(21) Appl. No.: 12/952,834

(22) Filed: Nov. 23, 2010

(65) Prior Publication Data
US 2012/0123415 A1   May 17, 2012

(30) Foreign Application Priority Data

Nov. 17, 2010  (EP) .................................... 10306265

(51) Int. Cl.
*A61B 17/70* (2006.01)
*A61B 17/74* (2006.01)
*A61B 17/17* (2006.01)

(52) U.S. Cl.
CPC ........ *A61B 17/742* (2013.01); *A61B 17/1721* (2013.01); *A61B 17/7098* (2013.01)

(58) Field of Classification Search
CPC ....... A61B 17/68; A61B 17/74–17/748; A61B 17/72; A61B 17/7208–17/725
USPC .............. 606/62–68; 403/252–254, 243, 289
See application file for complete search history.

(56) References Cited

U.S. PATENT DOCUMENTS

| 2,537,070 | A | * | 1/1951 | Longfellow | 606/67 |
| 3,433,220 | A | * | 3/1969 | Zickel | 606/67 |
| 3,579,831 | A | * | 5/1971 | Stevens et al. | 433/174 |
| 4,005,495 | A | * | 2/1977 | Locke et al. | 623/23.14 |
| 4,653,487 | A | * | 3/1987 | Maale | 606/62 |
| 4,653,489 | A | * | 3/1987 | Tronzo | 606/65 |
| 5,013,314 | A | * | 5/1991 | Firica | A61B 17/7208 606/104 |

(Continued)

FOREIGN PATENT DOCUMENTS

| EP | 0617927 | 10/1994 |
| WO | WO 01/54598 A1 | 8/2001 |
| WO | WO 2005/053545 A2 | 6/2005 |

OTHER PUBLICATIONS

European Search Report and Search Opinion dated Apr. 11, 2011 for corresponding European Patent Application 10306265.9 (with machine translation into English).

(Continued)

*Primary Examiner* — Jacqueline T Johanas
(74) *Attorney, Agent, or Firm* — Cooley LLP

(57) ABSTRACT

Devices, methods and systems for remedying or preventing fractures of the bone are disclosed. The devices, and corresponding methods and systems, may include first and second members each having a proximal end, a distal end and a middle portion and an outer surface. The first member may be configured to be positioned at least partially within the femoral neck of the femur. The second member may be configured to be oriented at an oblique angle relative to the first member and mechanically engaged with the first member through an interlocking connection between the distal end of the second member and the middle portion or the distal end of the first member.

15 Claims, 13 Drawing Sheets

(56) References Cited

U.S. PATENT DOCUMENTS

| | | | |
|---|---|---|---|
| 5,102,413 A * | 4/1992 | Poddar | 606/62 |
| 5,368,573 A * | 11/1994 | Andrew | 604/158 |
| 5,378,187 A * | 1/1995 | Forbes et al. | 446/268 |
| 5,514,137 A * | 5/1996 | Coutts | 606/62 |
| 5,531,748 A | 7/1996 | de la Caffiniere | |
| 5,743,912 A * | 4/1998 | Lahille et al. | 606/65 |
| 5,984,681 A * | 11/1999 | Huang | 433/174 |
| 6,056,749 A * | 5/2000 | Kuslich | 606/86 A |
| 6,079,075 A * | 6/2000 | Velez-Juan | 15/167.1 |
| 6,183,474 B1 * | 2/2001 | Bramlet et al. | 606/66 |
| 6,214,012 B1 | 4/2001 | Karpman et al. | |
| 6,221,074 B1 * | 4/2001 | Cole et al. | 606/62 |
| 6,237,183 B1 * | 5/2001 | Fischer | 15/167.1 |
| 6,375,659 B1 | 4/2002 | Erbe et al. | |
| 6,406,477 B1 * | 6/2002 | Fujiwara | 606/67 |
| 6,443,954 B1 | 9/2002 | Bramlet et al. | |
| 6,447,514 B1 | 9/2002 | Stalcup et al. | |
| 6,511,481 B2 | 1/2003 | von Hoffmann et al. | |
| 6,562,042 B2 | 5/2003 | Nelson | |
| 6,648,889 B2 * | 11/2003 | Bramlet et al. | 606/62 |
| 6,679,890 B2 | 1/2004 | Margulies et al. | |
| 6,709,185 B2 * | 3/2004 | Lefevre | 403/289 |
| 6,835,197 B2 | 12/2004 | Roth et al. | |
| 6,855,146 B2 | 2/2005 | Frigg et al. | |
| 6,887,243 B2 | 5/2005 | Culbert | |
| 6,890,333 B2 | 5/2005 | Von Hoffmann et al. | |
| 6,908,465 B2 | 6/2005 | Von Hoffmann et al. | |
| 7,182,765 B2 | 2/2007 | Roth et al. | |
| 7,258,692 B2 | 8/2007 | Thelen et al. | |
| 7,306,600 B2 | 12/2007 | Roth et al. | |
| 7,485,119 B2 | 2/2009 | Thelen et al. | |
| 7,488,320 B2 | 2/2009 | Middleton | |
| 7,488,329 B2 | 2/2009 | Thelen et al. | |
| 7,556,629 B2 | 7/2009 | Von Hoffmann et al. | |
| 7,645,280 B2 * | 1/2010 | Vaughan | 606/86 A |
| 7,713,290 B2 * | 5/2010 | Vaughan | 606/264 |
| 7,744,599 B2 * | 6/2010 | Cragg | 606/86 R |
| 7,909,825 B2 * | 3/2011 | Saravia | A61B 17/1725 606/63 |
| 8,062,270 B2 * | 11/2011 | Sweeney | 604/264 |
| 8,114,078 B2 * | 2/2012 | Aschmann | 606/64 |
| 8,137,350 B2 * | 3/2012 | Nakamura | 606/65 |
| 8,313,487 B2 * | 11/2012 | Tyber et al. | 606/62 |
| 8,486,071 B2 * | 7/2013 | Jensen | A61B 17/72 606/64 |
| 2002/0032445 A1 * | 3/2002 | Fujiwara | 606/67 |
| 2002/0156473 A1 * | 10/2002 | Bramlet et al. | 606/62 |
| 2002/0161445 A1 * | 10/2002 | Crozet | 623/17.11 |
| 2003/0045885 A1 * | 3/2003 | Margulies et al. | 606/94 |
| 2003/0065329 A1 * | 4/2003 | Vaughan | 606/61 |
| 2004/0002759 A1 * | 1/2004 | Ferree | 623/17.11 |
| 2004/0193161 A1 * | 9/2004 | Vaughan | 606/61 |
| 2004/0254578 A1 * | 12/2004 | Vaughan | 606/61 |
| 2005/0010226 A1 * | 1/2005 | Grady et al. | 606/69 |
| 2005/0047853 A1 * | 3/2005 | Pettitt et al. | 403/289 |
| 2005/0070903 A1 | 3/2005 | Roth et al. | |
| 2005/0131411 A1 | 6/2005 | Culbert | |
| 2005/0137595 A1 | 6/2005 | Hoffmann et al. | |
| 2005/0171544 A1 * | 8/2005 | Falkner, Jr. | 606/69 |
| 2005/0187550 A1 * | 8/2005 | Grusin | 606/62 |
| 2006/0015188 A1 * | 1/2006 | Grimes | A61B 17/1668 623/23.19 |
| 2006/0084999 A1 * | 4/2006 | Aschmann | 606/64 |
| 2006/0089642 A1 * | 4/2006 | Diaz et al. | 606/60 |
| 2006/0149362 A1 * | 7/2006 | Pedrozo et al. | 623/1.35 |
| 2006/0189991 A1 * | 8/2006 | Bickley | 606/72 |
| 2007/0083265 A1 * | 4/2007 | Malone | 623/17.11 |
| 2007/0123995 A1 | 5/2007 | Thelen et al. | |
| 2007/0162012 A1 | 7/2007 | Roth et al. | |
| 2007/0225714 A1 | 9/2007 | Gradl et al. | |
| 2007/0225721 A1 | 9/2007 | Thelen et al. | |
| 2007/0270848 A1 * | 11/2007 | Lin | 606/65 |
| 2007/0293861 A1 * | 12/2007 | Rezach et al. | 606/61 |
| 2008/0077140 A1 * | 3/2008 | Osman | 606/62 |
| 2008/0140077 A1 * | 6/2008 | Kebaish | 606/64 |
| 2008/0188853 A1 * | 8/2008 | Ferrante et al. | 606/62 |
| 2008/0234737 A1 * | 9/2008 | Boschert | 606/254 |
| 2008/0262497 A1 * | 10/2008 | Nijenbanning et al. | 606/63 |
| 2008/0281326 A1 * | 11/2008 | Watanabe et al. | 606/62 |
| 2008/0306553 A1 * | 12/2008 | Zucherman et al. | 606/301 |
| 2008/0319435 A1 * | 12/2008 | Rioux et al. | 606/33 |
| 2009/0062796 A1 * | 3/2009 | Parks et al. | 606/62 |
| 2009/0069813 A1 | 3/2009 | Von Hoffmann et al. | |
| 2009/0157078 A1 * | 6/2009 | Mikol | 606/62 |
| 2009/0198237 A1 | 8/2009 | Downey et al. | |
| 2009/0204117 A1 | 8/2009 | Middleton | |
| 2009/0228008 A1 * | 9/2009 | Justin et al. | 606/62 |
| 2009/0287213 A1 * | 11/2009 | Pieske | 606/62 |
| 2009/0306666 A1 * | 12/2009 | Czartoski | A61B 17/72 606/64 |
| 2010/0016983 A1 | 1/2010 | Smit | |
| 2010/0023011 A1 | 1/2010 | Nakamura et al. | |
| 2010/0023064 A1 * | 1/2010 | Brunger et al. | 606/308 |
| 2011/0022066 A1 * | 1/2011 | Sevrain | 606/151 |
| 2011/0054474 A1 * | 3/2011 | Metzinger et al. | 606/64 |
| 2011/0137313 A1 * | 6/2011 | Jensen | A61B 17/72 606/64 |
| 2011/0196369 A1 * | 8/2011 | Osman | 606/62 |
| 2011/0282398 A1 * | 11/2011 | Overes et al. | 606/304 |
| 2012/0059376 A1 * | 3/2012 | Rains et al. | 606/62 |
| 2012/0130370 A1 * | 5/2012 | Kinmon | 606/62 |

OTHER PUBLICATIONS

Official Action dated Apr. 10, 2013 for corresponding European Patent Application No. 10306265.9 (with machine translation into English).

Official Action dated Oct. 17, 2013 for corresponding European Patent Application No. 10306265.9 (with machine translation into English).

English Translation of International Search Report dated Feb. 9, 2012 for corresponding International Patent Application No. PCT/FR2011/052664.

English Translation of Written Opinion dated May 17, 2013 for corresponding International Patent Application No. PCT/FR2011/052664.

English Translation of International Preliminary Report on Patentability dated May 21, 2013 for corresponding International Patent Application No. PCT/FR2011/052664.

* cited by examiner

DEVICES, METHODS AND SYSTEMS FOR REMEDYING OR PREVENTING FRACTURES

CROSS-REFERENCE TO RELATED APPLICATIONS

This application claims priority under Title 35, United States Code, § 119(a)-(d) to European Patent Application No., EP 10306265.9, filed on Nov. 17, 2010, the disclosure of which is incorporated herein by reference.

FIELD

Devices, methods and systems for preventing and/or treating hip fractures are described herein. In particular, an implant effective for augmenting the strength of a hip joint and having a first component and a second component mechanically connected within the proximal end of the femur is provided. More particularly, a prophylactic device having a first member inserted into the femoral neck of the femur and second member inserted below the first member and in interlocking engagement with the first member, and corresponding methods for mechanically engaging the first and second members, are described herein.

BACKGROUND

In their most basic construct, bones are formed of a relatively soft, spongy cancellous bone having a high degree of visible porosity, which is surrounded by a much more rigid and dense material called the cortex, or cortical bone. The cancellous bone yields under relatively low loading, while the much denser cortical bone supports much higher loading.

One of the most heavily-stressed, load-carrying bone joints in the human body is the hip joint. The hip joint is essentially a ball and socket mechanism formed between the pelvic bone and the proximal end of the femur. The femur, otherwise known as the thigh bone, generally comprises an elongate shaft extending from the pelvis to the knee. The proximal end of the femur includes a head, a neck and greater and lesser trochanter regions that connect the femoral head and neck to the shaft of the femur, as shown in FIG. 1. Generally speaking, the trochanter region holds the femoral head and neck at an angle of about 130 degrees relative to the femur shaft.

While the femur is generally reputed to be the longest and strongest bone in the human skeleton, the proximal end of the femur is particularly susceptible to the onset of osteoporosis, which severely compromises the strength of the hip joint. Osteoporosis is a metabolic disease characterized by a decrease in bone mass and bone structure impairment and, leads to skeletal fractures under light to moderate trauma and, in its advanced state, can lead to fractures under normal physiologic loading conditions. Common fracture sites include the hip, wrist and vertebrae. Hip fractures generally occur in one of two primary areas—the femoral neck or the trochanter regions. Common fractures in the femoral neck and the trochanter regions include subcapital neck fractures, transcervical neck fractures, intertrochanteric neck fractures, subtrochanteric neck fractures, greater trochanter fractures and lesser trochanter fractures, as shown in FIG. 2.

While osteoporosis can affect persons of all ages and regardless of gender, it is especially prevalent in the elderly population. Femoral neck fractures are a major source of morbidity and mortality in elders. A very high percentage of all hip fractures occur in people over the age of fifty. During the aging process, in general, endosteal and outer periosteal diameters increase as a protective mechanism. As the bone mass shifts further from the epicenter, skeletal strength is maximized despite a decrease in bone mass. Similar protective mechanisms, however, do not occur in areas of cancellous bone, such as in the femoral neck. Because the femoral neck naturally has low levels of periosteum, this area of the femur is unable to compensate for the loss of endosteal bone by periosteal bone formation. When an elderly patient falls, some amount of energy is dissipated. Most of the energy in a fall is absorbed by active muscle contractions. However, in an elderly patient, the neuromuscular response often cannot act quickly enough to dissipate this kinetic energy and, instead, it gets transferred to the femoral neck. Consequently, because the femoral neck can only absorb a portion of that energy, the level of stored energy in the femoral neck often exceeds its threshold when an elderly person falls and a fracture develops.

While the femoral neck clearly poses a difficult problem to the elderly patient, it also poses a significant challenge to orthopedic surgeons and others skilled in the art seeking to mitigate the number of such occurrences and subsequent hospitalizations. Due to an increase in the elderly population, the number of cases and hospitalizations has been exacerbated. As a result, medical costs from such hip fractures place a significant strain on what many consider to be an already over-extended healthcare system.

Prior art devices and procedures relating to hip fractures generally focus on repairing hip fractures by reducing, compressing and stabilizing the cracked or broken portion of the bone. Traditional devices for treating a hip fracture comprise an intramedullary nail positioned within the intramedullary canal of the femur and configured for mechanical connection with a hip screw oriented in a position that is substantially parallel to the longitudinal axis of the femoral neck. One or more external plates are also often added for additional support and stability. Exemplary configurations are disclosed in U.S. Pat. No. 5,531,748 to de la Caffinierre, U.S. Pat. No. 6,443,954 to Bramlet et al., U.S. Pat. No. 6,511,481 to von Hoffmann et al., U.S. Pat. No. 6,562,042 to Nelson and U.S. Pat. No. 6,855,146 to Frigg et al. Some conventional designs may also inject a flowable material, such as bone cement, to further stabilize the device within the bone, as discussed in U.S. Pat. No. 7,488,320 to Middleton.

Surprisingly, however, few attempts have been made to develop devices and methods aimed at preventing hip fractures from occurring in the first place. There exist no standard procedures employed by doctors and others skilled in the art for augmenting the femoral neck to guard against future trauma to the hip joint. Over the past 50 years, very few investigations into prophylactic strengthening of an intact femoral neck have been reported. In 1960, G. S. Crockett suggested positioning a single pin in the femoral neck to strengthen the neck axis against shear stresses. In 2001, Franz et al. investigated the augmentation effects of injecting low-viscosity bone cement into the proximal end of the femur. Most recently, U.S. Pat. No. 6,679,890 to Marguiles et al. has disclosed a "hybrid technique" that uses a single implant component in combination with cement injection. The '890 patent inserts a hollow implant into the femur along the longitudinal axis of the femoral neck and thereafter fills the implant and the surrounding bone with cement. The "hybrid technique" of the '890 patent focuses on using bone cement to form a union between a single implant component and surrounding cancellous bone.

Accordingly, there currently exist no devices, methods or systems in the prior art directed to the prophylactic strengthening of an intact bone, such as the femur and particularly the femoral neck, using multiple supporting and augmentative implant components and which does not require the use of a flowable material.

SUMMARY

Novel embodiments of devices for preventing or treating bone fractures, as well as corresponding methods and systems, are described herein. Some embodiments of the present disclosure are directed to a medical device for remedying and/or preventing fractures in the femur. The medical device may include a first member having a proximal end, a distal end, a middle portion and an outer surface, and being configured to be positioned at least partially within the femoral neck of the femur, and a second member having a proximal end, a distal end, a middle portion and an outer surface, and being configured to be positioned at least partially within the shaft of the femur and oriented at an oblique angle relative to the first member. In some embodiments, the distal end of the second member may be configured for interlocked engagement with the middle portion or distal end of the first member. The first member may include an inner lumen, an outer surface and a plurality of openings, wherein the inner lumen may be configured to receive a flowable material and the plurality of openings may be configured to enable the flowable material to flow from the inner lumen to at least the outer surface of the first member. According to some embodiments, the second member may include an inner lumen, an outer surface and a plurality of openings, wherein the inner lumen may be configured to receive a flowable material and the plurality of openings may be configured to enable the flowable material to flow from the inner lumen to at least the outer surface of the second member. In some embodiments, both the first and second members may include an inner lumen, an outer surface and a plurality of openings, wherein the inner lumen may be configured to receive a flowable material and the plurality of openings may be configured to enable the flowable material to flow from the inner lumen to at least the outer surface of the first and second members.

The device embodiments may include various engagement mechanisms. In some embodiments, the first member may be configured with a plurality of lateral planes and the distal end of the second member may be configured with a plurality of tabbed blades that engage with the lateral planes of the first member to provide the interlocked engagement between the first member and the second member. The first member may also be configured with a through-hole and the distal end of the second member may be configured with a plurality of tabbed blades that engage with the through-hole of the first member to provide the interlocked engagement between the first member and second member. Furthermore, the first member may be configured with a threaded hole and the distal end of the second member may be configured with a threaded tip that threadably engages with the threaded hole of the first member to provide the interlocked engagement between the first member and the second member. According to some embodiments, the first member may be configured with a through-hole and the distal end of the second member may be tapered to provide for a press fit of the second member within the through-hole of the first member to provide the interlocked engagement between the first member and the second member.

In some embodiments, at least one of the first member or the second member may include a rod having a threaded portion configured with external threads and a tube having an inner lumen configured with internal threads for mating engagement with the external threads of the rod, wherein the rod moves linearly within the tube upon being rotated relative to the tube to provide for adjustment of the length of the first member or second member.

Device embodiments of the present disclosure may have various features. For example, the oblique angle may be within the range of 91 to 179 degrees. Moreover, at least a portion of the outer surface of at least one of the first member or the second member may be configured with threads, longitudinal grooves, circumferential grooves, may be partially or fully knurled and/or include a bioactive coating. In some embodiments, at least a portion of the first member may have a generally cylindrical shape and another portion of the first member may have a shape selected from the group of shapes consisting of an oval, star, diamond, square and rectangle. The first member may be oriented in the femoral neck of the femur in a position substantially parallel to the longitudinal axis of the femoral neck, according to some embodiments.

The present disclosure is also directed to medical devices for remedying and/or preventing fractures in the femur that include a first member having a proximal end, a distal end, and a middle portion and an outer surface, and being configured to be positioned at least partially within the femoral neck of the femur and a second member having a proximal end, a distal end, and a middle portion and an outer surface, and being configured to be positioned at least partially in the shaft of the femur and oriented at an oblique angle relative to the first member, wherein the distal end of the second member includes an opening configured to receive and maintain the first member in a predetermined location along the length of the first member and to provide for interlocked engagement between the first member and the second member. The first member may include an inner lumen, an outer surface and a plurality of openings, wherein the inner lumen may be configured to receive a flowable material and the plurality of openings may be configured to enable the flowable material to flow from the inner lumen to at least the outer surface of the first member. According to some embodiments, the second member may include an inner lumen, an outer surface and a plurality of openings, wherein the inner lumen may be configured to receive a flowable material and the plurality of openings may be configured to enable the flowable material to flow from the inner lumen to at least the outer surface of the second member. In some embodiments, both the first and second members may include an inner lumen, an outer surface and a plurality of openings, wherein the inner lumen may be configured to receive a flowable material and the plurality of openings may be configured to enable the flowable material to flow from the inner lumen to at least the outer surface of the first and second members.

In some device embodiments, the first member may be configured with a through-hole and the distal end of the second member may be tapered to provide for a press fit of the second member within the through-hole of the first member to provide the interlocked engagement between the first member and the second member.

In some embodiments, at least one of the first member or the second member may include a rod having a threaded portion configured with external threads and a tube having an inner lumen configured with internal threads for mating engagement with the external threads of the rod, wherein the rod moves linearly within the tube upon being rotated relative to the tube to provide for adjustment of the length of the first member or second member.

Device embodiments of the present disclosure may have various features. For example, the oblique angle may be within the range of 91 to 179 degrees. Moreover, at least a portion of the outer surface of at least one of the first member or the second member may be configured with threads, longitudinal grooves, circumferential grooves, may be partially or fully knurled and/or include a bioactive coating. In some embodiments, at least a portion of the first member may have a generally cylindrical shape and another portion of the first member may have a shape selected from the group of shapes consisting of an oval, star, diamond, square and rectangle. The first member may be oriented in the femoral neck of the femur in a position substantially parallel to the longitudinal axis of the femoral neck, according to some embodiments.

Device embodiments of the present disclosure may also be directed to medical devices for remedying and/or preventing fractures in a long bone of a human body. These devices may include a first member having a proximal end, a distal end, a middle portion, an inner lumen, an outer surface, and a plurality of openings, wherein the inner lumen may be configured to receive a flowable material, the plurality of openings may be configured to enable the flowable material to flow from the inner lumen to at least the outer surface, and the first member may be configured to be positioned in the long bone and oriented generally perpendicular long axis of the long bone. Some embodiments may further include a second member having a proximal end, a distal end, a middle portion, an inner lumen, an outer surface, and a plurality of openings, wherein the inner lumen may be configured to receive a flowable material, the plurality of openings may be configured to enable the flowable material to flow from the inner lumen to at least the outer surface, and the second member may be configured to be positioned in the long bone and oriented at an oblique angle relative to the first member. In some embodiments, the distal end of the second member is configured to be received in interlocked engagement within the middle portion or the distal end of the first member.

Some embodiments of the present disclosure may be directed to methods for remedying and/or preventing fractures in the femur that include forming a first member pilot hole at least partially within the femoral neck of the femur, the first member pilot hole being configured to receive a first member of an implant device; forming a second member pilot hole in a position within the femur that is oriented at an oblique angle to the first member pilot hole and below the first member pilot hole, the second member pilot hole intersecting the first member pilot hole and being configured to receive a second member of the implant device; inserting the first member into the first member pilot hole; inserting the second member into the second pilot hole towards the first member; and engaging a distal end of the second member with the middle portion or the distal end of the first member to provide interlocking engagement between the first member and the second member.

In some method embodiments, the first member may include a proximal end, a distal end, an inner lumen, an outer surface and a plurality of openings and an injection device may inserted into the inner lumen of the first member to provide for the injection of flowable material into the inner lumen and through one or more of the plurality of openings of the first member to at least the outer surface of the first member. In some embodiments, the second member may include a proximal end, a distal end, an inner lumen, an outer surface and a plurality of openings and an injection device may be inserted into the inner lumen of the second member to provide for the injection of flowable material into the inner lumen and through one or more of the plurality of openings of the second member to at least the outer surface of the second member. In some method embodiments, both the first and second members may include an inner lumen, an outer surface and a plurality of openings and an injection device may inserted into the inner lumen of either or both of the first and second members to provide for the injection of flowable material into the inner lumen and through one or more of the plurality of openings of the first and/or second member.

Some method embodiments may include inserting the injection device into the first member or the second member such that an injection tip of the injection device is positioned at the distal end of the first or second member, injecting flowable material into the first or second member, moving the injection device toward the proximal end of the first or second member during the injection of the flowable material and thereafter ceasing injection when the injection tip is at the proximal end of the first or second member.

The method embodiments may be directed to various ways of engagement the first and second members. In some embodiments, engaging a distal end of the second member with the middle portion or the distal end of the first member may include engaging a plurality of lateral planes configured on the first member with a plurality of tabbed blades configured at the distal end of the second member. In some method embodiments, engaging a distal end of the second member with the middle portion or the distal end of the first member may include engaging a through-hole of the first member with a plurality of tabbed blades configured at the distal end of the second member. In some embodiments, engaging a distal end of the second member with the middle portion or the distal end of the first member may include engaging a threaded hole of the first member with threaded tip configured at the distal end of the second member. In some embodiments, engaging a distal end of the second member with the middle portion or the distal end of the first member may include engaging a through-hole of the first member with a tapered portion of the second member.

The foregoing and other features, aspects and advantages of the disclosed embodiments, along with the claimed embodiments themselves, will be more apparent from the accompanying figures, detailed description and claims.

BRIEF DESCRIPTION OF THE FIGURES

FIG. 5b shows a top plan view of an embodiment of the first component of the implant depicted in FIG. 5a.

FIG. 5c shows an elevational view of the first component of the implant depicted in FIG. 5a.

FIG. 5d shows an elevational view of an embodiment of the second component of the implant depicted in FIG. 5a.

FIG. 6b shows an elevational view of an embodiment of the second component of the implant depicted in FIG. 6a.

FIG. 7b an elevational view of an embodiment of the second component of the implant depicted in FIG. 7a.

DETAILED DESCRIPTION

Figure 1:
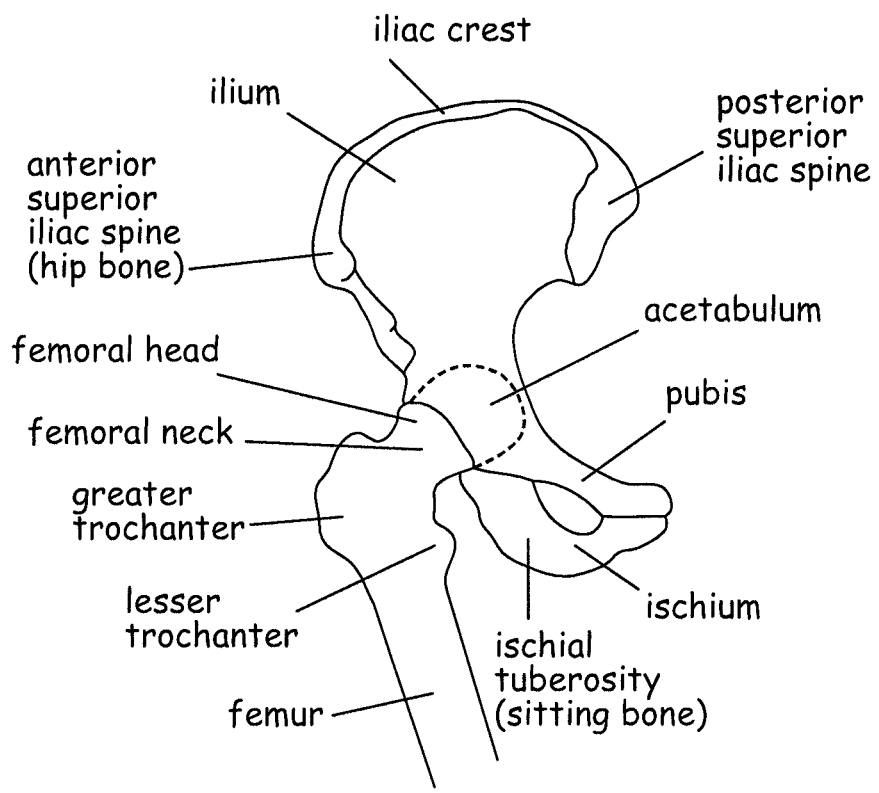
FIG. 1 depicts a hip joint and, in particular, the ball-and-socket connection between the proximal end of the femur and the pelvic bone.
Figure 2:
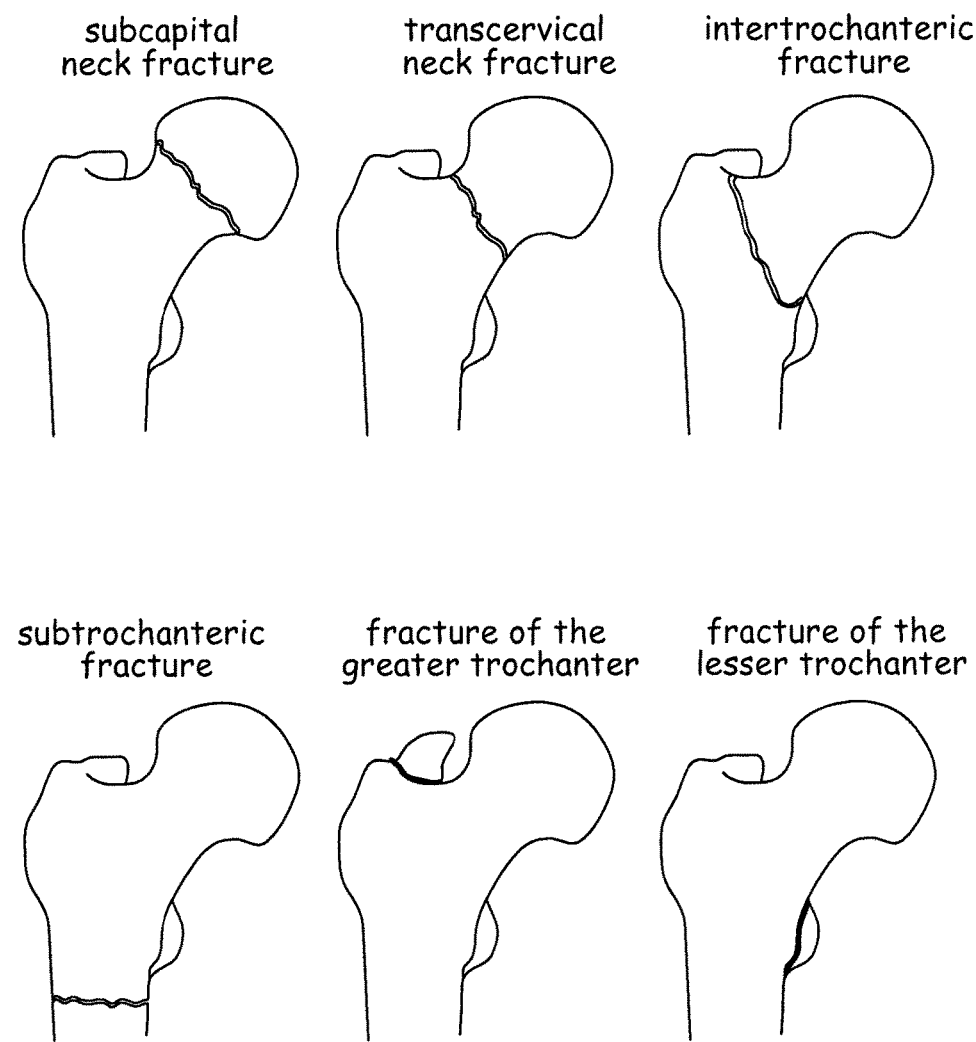
FIG. 2 depicts various examples of fractures that commonly occur in the femoral neck and trochanter regions.

Embodiments of the present disclosure are directed to implants, and corresponding methods and systems, for preventing or remedying fractures in mammalian bone. In some exemplary embodiments, the implants may be useful for preventing or treating fractures occurring in the femur or other long bones of a human being. The implants disclosed herein may be configured to be particularly useful as a device for preventing fractures of the hip bone, such as breaks or cracks in the femoral neck, femoral head or trochanter regions located in the proximal end of the femur.

The implants of the present disclosure are described herein primarily in the context of preventing and/or treating fractures occurring in the proximal end of the femur. However, the implants and corresponding methods and systems disclosed herein may be useful and applicable in a variety of different medical settings. For example, fractures of the fibular and tibial malleoli, pilon fractures and other fractures of the bones of the leg may be prevented and/or treated using various configurations of the implants of the present disclosure.

Other than preventing and/or treating fractures relating to the hip joint, the implants of the present disclosure may be configured to assist in preventing and/or treating fractures relating to the hand, including without limitation, interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation and phalangeal and metacarpal osteotomy fixation. Similarly, a wide variety of phalangeal and metatarsal problems, such as ossification and/or fracture, relating to the foot may also be treated using customized configurations of the implants of the present disclosure, including without limitation, distal metaphyseal osteotomies, base wedge osteotomies, oblique diaphyseal and digital arthrodesis. The implants, and corresponding methods and systems, may also be used in conjunction with one or more plates and/or washers, depending upon the particular embodiments.

Implant configurations of the present disclosure may also be used to attach tissue or structure to the bone, such as in ligament reattachment and other soft tissue attachment procedures. In some embodiments, the implants may also be used to attach sutures to the bone, such as in any of a variety of tissue suspension procedures. For example, peripheral applications for some embodiments of the implants may include use for fastening soft tissue, such as capsule, tendon or ligament, to the bone. Some embodiments may also be used to attach a synthetic or allograft material to the bone.

Some embodiments of the implants of the present disclosure may also be used to assist in administering medication locally. For example, some embodiments of the implants may be partially or fully cannulated, as explained in more detail herein, and thus configured to accept an antibiotic impregnated rod for the slow adsorption of medication locally. Alternatively, medication may be mixed into a flowable material that is injected into certain implant device embodiments. Such embodiments may be particularly beneficial to prevent infection during implantation of the devices of the present disclosure or when osteomyelitis exists.

Embodiments of the present disclosure may also provide for implant kits, which may be assembled for field use by hospitals, physicians in private practice, the military, sports medicine and/or paramedical personnel. The kits may be configured to contain one or more implants and appropriate surgical instrumentation, including without limitation, a guide, trocar, drill, sextant and/or other tools required or useful for installing the implants. Some kit embodiments may also include sterilization or disinfectant materials, a skin stapler, bandages, gloves and/or antibiotics for wound prophylaxis.

Figure 3:
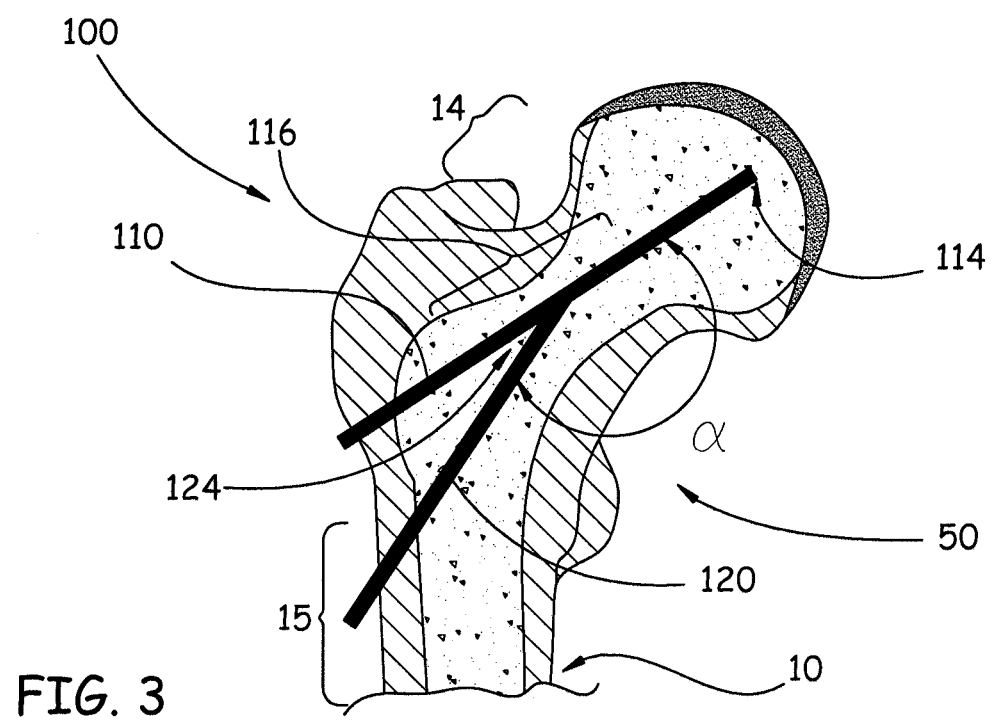
FIG. 3 shows a basic configuration of an implant having a first component and second component and positioned in the proximal end of the femur, according to some embodiments described herein.

FIG. 3 shows a basic configuration of an embodiment of an implant (100) for preventing or treating a fracture in the proximal end (50) of the femur (10) according to the present disclosure. Embodiments of the implant (100) according to the present disclosure contemplate a two-piece device having a first component (110) and a second component (120). In some embodiments, the first component (110) may be inserted into the trabecular (i.e., cancellous or spongy) bone portion of the femoral neck (14) of the femur (10) in a direction that is substantially parallel to the longitudinal axis of the femoral neck (14). In some embodiments, the first component (110) may be inserted into the femoral neck (14) of the femur (10) in a direction oblique or otherwise non-parallel to the longitudinal axis of the femoral neck (14). To this end, the second component (120) may be inserted upwardly through the shaft (15) of the femur (10) at an angle, a relative to the first component (110), as shown in FIG. 3. As also shown, the proximal end of the second component (i.e., the end of the second component 120 opposite distal end 124), can intersect with the cortical bone of the long bone of the femur (see FIG. 3, crosshatching representing cortical bone), and may protrude therefrom; additionally, the proximal end of the first component 110 (the end of the first component opposite distal end 114) can also intersect with the cortical bone and may protrude therefrom. In addition, as shown, the proximal end of the second component may be positioned at a distance further from the femoral head than that of the proximal end of the first component. As also shown in FIG. 3, a longitudinal axis of the first component forms a first angle with the long axis of the long bone, and a longitudinal axis of the second component forms a second angle with the long axis of the long bone which is greater than the first angle.

For sake of clarity, the term "first component" will be used throughout this disclosure to refer to the component depicted in the figures as that which is positioned at least partially within the femoral neck (14) of the femur (10) generally parallel to the longitudinal axis of the femoral neck (i.e., orientations of the first component that are non-parallel to the longitudinal axis of the femoral neck are also contemplated). The term "second component" will be used throughout this disclosure to refer to the component depicted in the figures as that which is positioned at least partially within the shaft (15) of the femur (10) below and at an oblique angle to the first component in a relatively vertical orientation. The first and second components and their corresponding descriptions provided herein may be interchangeable depending on the embodiment and are not limited to the specific configurations described herein.

Figure 4:
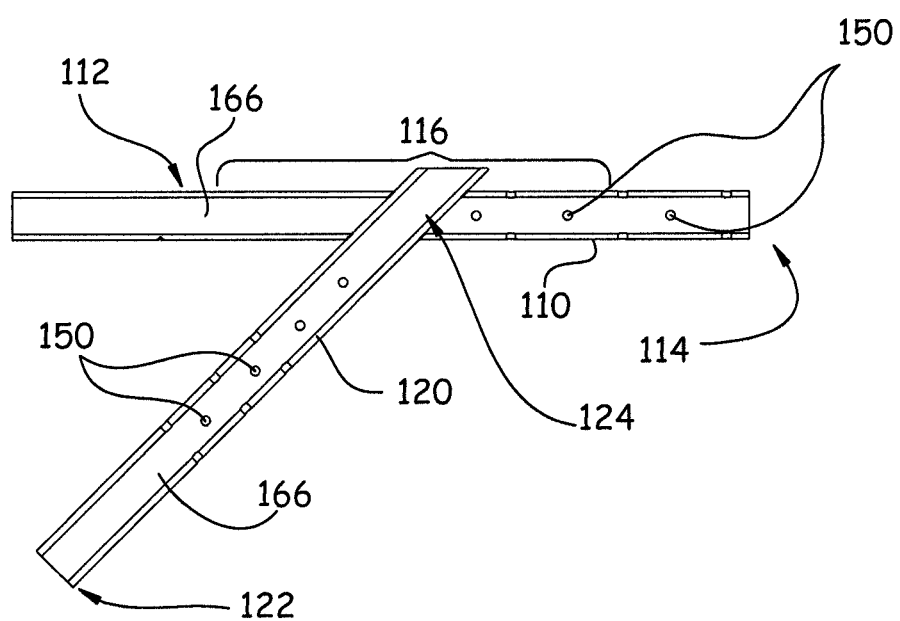
FIG. 4 shows a cross-sectional view of a basic configuration of an implant having a first component and second component, where both components are cannulated for receiving a flowable material and contain a plurality of holes for diffusing such material into surrounding bone following implantation, according to some embodiments described herein.

In some embodiments, the components (110, 120), upon being inserted into the femur (10), may be configured to engage with one another, in situ and in interlocking mechanical connection, to form a single, monobloc structure within the femur (10), as generally shown in FIG. 3. This engagement may occur at various locations along the first component (110) and generally toward the distal end (124) of the second component (120). As shown in FIG. 4, the distal end (124) of the second component (120) may be mechanically engaged with the first component (110) toward a middle portion (116) of the first component (110). In other embodiments, the distal end (124) of the second component (120) may be engaged at either the distal end (114) or the proximal end (112) of the first component (110). Embodiments of the present disclosure also contemplate various possible mechanical connections for establishing an interlocking engagement between the first component (110) and the second component (120). Such connections may include, without limitation, (i) snap-fitting a pair of tabbed blades over a planar surface or within a through-hole, (ii) threading a threaded tip into a threaded hole and/or (iii) press-fitting one component into a through-hole of the other.

Upon being mechanically connected with one another in interlocking engagement, the components (110, 120) may form an implant (100), as shown in FIG. 4, having a generally "Y"-shaped configuration that serves to anchor the implant (100) securely in the proximal end (50) of the femur (10), as shown in FIG. 3. The "Y" shape provided by the mechanical joining of the first component (110) and second component (120) may be configured so as to form an angle, α, between the two components (110, 120). The angle, α, which represents the angle at which the second component (120) is inserted and positioned in the femur (10) relative to the first component (110), may be any angle between 0 and 180 degrees, depending upon the particular application and desired objectives. In some embodiments of the present disclosure, the angle α may be any oblique angle between 91 and 179 degrees.

The first component (110) and the second component (120) may each have a wide variety of structural configurations and features, depending upon the particular embodiment of the implant (100). Each component (110, 120) may have a proximal end, distal end and a middle portion. In some embodiments, the two components (110, 120) may be generally cylindrical in shape and have similar or near-identical structural characteristics. Other embodiments of the implant (100) may be directed to configurations where the first component (110) is cylindrical and the second component (120) is non-cylindrical, or vice versa. In some embodiments, both components (110, 120) may be non-cylindrical, e.g., oval, star-shaped or rectangular. In some embodiments, a single component (110 or 120) may comprise more than one shape, for example, the first third of the component's length may be cylindrical and then transition into an oval or rectangular shape for the remaining length of the component. Some component embodiments may comprise several different shapes. For sake of clarity, the embodiments discussed herein are generally described in terms of "diameter"; however, this does not serve to limit the present disclosure to cylindrical configurations to the exclusion of non-cylindrical configurations. In some embodiments, either or both components may comprise grooves traversing a portion or the entire circumference of the component along some or all of the length of such component. The circumferential grooves may be of any suitable shape, including without limitation, V-shaped and/or square or rectangular. In some embodiments, either or both of the components (110, 120) may contain one or more longitudinal grooves traversing some or all of the length of the component(s). The longitudinal grooves may be substantially parallel to the longitudinal axis of the component(s) or may traverse the length of the component(s) in a helical- or spiral-type manner. The longitudinal grooves may be of any suitable shape, including without limitation, V-shaped and/or square or rectangular. The first component (110) and the second component (120) may be comprised of any suitable material or combination of materials, including without limitation, titanium, stainless steel and/or polyether ether ketone ("PEEK").

Figure 10:
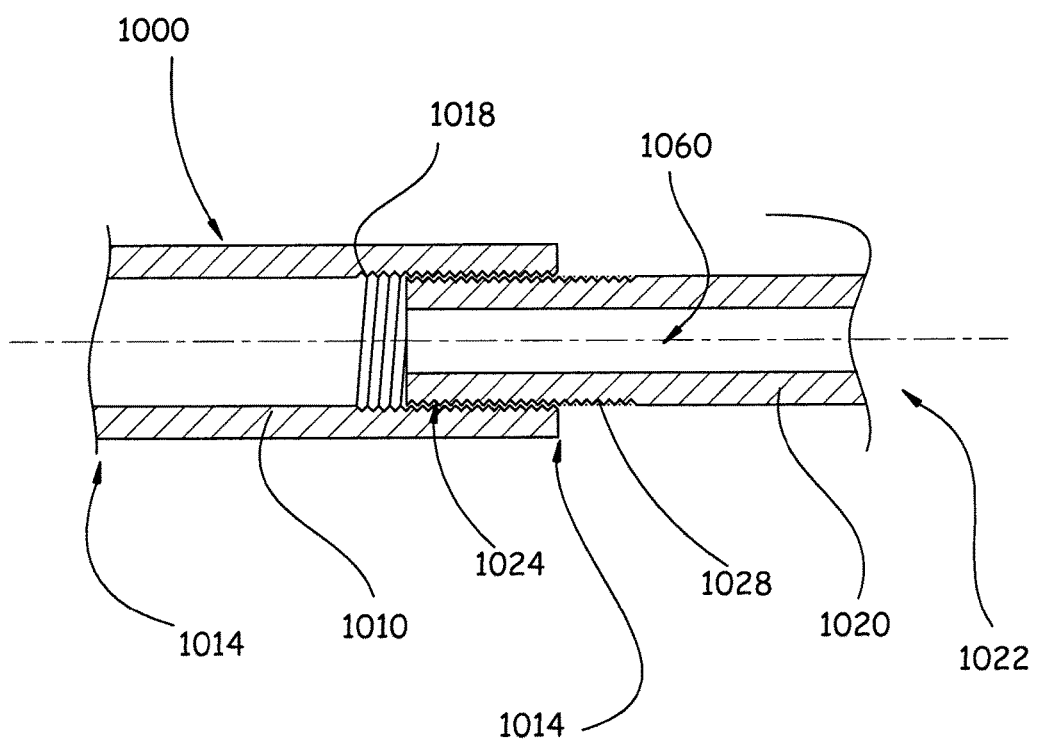
FIG. 10 shows a cross-sectional view of a component of an implant, where the component is configured with a two-part structure for adjusting the length of the component, according to some embodiments described herein.

The respective lengths of the first component (110) and/or the second component (120) may vary depending upon the particular application for the implant (100). For embodiments configured for use in preventing fractures in the proximal end (50) of the femur (10), a length of 50 to 150 millimeters ("mm"), for example, may be used. The components (110, 120) do not have to be the same shape or length. The first and second components (110, 120) may be manufactured and used in a variety of shapes and lengths, depending upon the application. In some embodiments, the length of either or both components (110, 120) may be adjusted before during and/or after implantation by configuring one or both ends of either component (110, 120) with one or more grooves, as shown in FIG. 7b at reference numeral 718, which allow for component to be snapped or otherwise broken-off. The grooves may traverse the circumference of the component in whole or in part. In some embodiments, the length of the components (110, 120) may be adjusted before, during and/or after implantation by configuring the component as a two-part structure adjustable in length by threading and unthreading one part relative to the other, as shown in FIG. 10 and discussed herein below.

The components may also be provided with any suitable diameter. For embodiments configured for use in preventing fractures in the proximal end (50) of the femur (10), the components may be configured with an outer diameter of 3 to 15 mm, or at least any diameter that is compatible with applicable surgical instrumentation. The outer surface of the components (110, 120) may be smooth for easily inserting the components (110, 120) by pushing or lightly impacting. In some embodiments, the outer surface of either or both components (110, 120) may contain threads along some or all of its length to provide for threaded insertion and improved anchorage in the bone (see FIGS. 6*a*-6*c*). In some embodiments, the outer surface of the components (110, 120) may be coated with a material promoting anchorage of the component(s) within the femur, including without limitation, hydroxyapatite. In some embodiments, the outer surface of the components (110, 120) may be partially or fully knurled to improve and/or promote anchorage of the component(s) within the femur. The distal end of each component may also be configured to have a rounded (see FIG. 7*a*) or chamfered (see FIG. 7*a*) tip, depending on the particular embodiment of the present disclosure.

In some embodiments, either or both of the components (110, 120) may be hollow (i.e., cannulated) along their entire length so as to form an inner lumen (166) that extends from a proximal end to a distal end of the cannulated component. Alternatively, in some embodiments of the present disclosure, one or both of the components (110, 120) may only be partially cannulated. In other embodiments, one or both of the components (110, 120) may be completely solid.

When a component is fully or partially cannulated, some embodiments of the present disclosure contemplate injecting flowable material into one or both of the components (110, 120). Such flowable material may include, without limitation, bone cement. The wall thickness of a fully or partially cannulated component may be any suitable thickness. For embodiments configured for use in preventing fractures in the proximal end (50) of the femur (10), a component wall thickness of approximately 0.1 to 5 mm may be used. In some embodiments having one or more fully or partially cannulated components, it may also be possible to configure the walls of one or both of the components with one or more holes (150), as shown in FIG. 4 in a uniform manner or in random locations. The holes may be circular, oval, oblong, square or any other suitable shape. The holes also may be positioned longitudinally or peripherally along the component, as shown in FIG. 4. When flowable material (i.e., bone cement/filler) is injected into a component having these holes, the material is able to flow through the holes and into the surrounding cancellous bone. The holes provide controlled diffusion of the material into the surrounding cancellous bone and, upon the material hardening, create an interlocking anchor that improves the fixation of the components within the bone.

In some embodiments, the injection of flowable material may begin at a distal end of either component (110, 120) by positioning an injection device (e.g., an injection cannula) into the component and, in particular, positioning an injection tip of the device at the distal end of the component. As flowable material is injected into the component and through the one or more holes (150), the injection device may be gradually pulled out of the component until the injection tip of the injection device is positioned at the proximal end of the component. In some embodiments, both components (110, 120) may be filled at the same time.

Implanting the implant (100) into the bone may be accomplished using a variety of known surgical techniques. The following methods are merely exemplary and in the specific context of a femoral neck implant. In some embodiments, an implantation axis for the first component (110) may first be identified using a guide instrument to define the position of where the implant is to be inserted using, for example, double fluoroscopy in an orthogonal plane. Depending on the embodiment, the implantation axis may be substantially centered within the cross-sectional area of the femoral neck (14), i.e., substantially along the longitudinal axis of the femoral neck (14), or may be positioned off-center so as to be adjacent to the longitudinal axis of the femoral neck. In some embodiments, the implantation axis may be parallel or nonparallel to the longitudinal axis of the femoral neck (14). In some embodiments, a trocar may also be positioned up against the bone to protect surrounding soft tissues (e.g., the skin or muscles) at the location where a pilot hole for the first component (110) is to be drilled. Using an appropriate surgical drill and corresponding drill bit, a pilot hole of appropriate diameter for receiving the first component (110) may be made into the proximal end of the femur, through the trochanter region and into the femoral neck (14) to a specified depth. In some embodiments, the depth of the pilot hole for the first component (110) may be such that the distal end (114) of the first component (110) is between 1 mm and 15 mm from the end of the femoral head, to ensure that the first component (110) does not protrude through the bone. After debris is removed from the pilot hole, the first component (110) may be inserted. In some embodiments, the pilot hole for the second component (120) may be drilled first.

Using the pilot hole of first component (110) as a reference, a sextant may be used to identify an axis of insertion for the second component (120). In those embodiments where the pilot hole for the second component (120) is drilled first, a sextant may be used to identify an axis of insertion for the first component (110). In some embodiments, namely those wherein the first component (110) and the second component (120) are joined in situ in interlocking engagement, the axis of insertion for the second component (120) should be positioned so as to intersect that portion of the axis of insertion of the first component (110) that will allow the second component (120) and the first component (110) is to be mechanically connected. Following identification and alignment of the axis of insertion for the second component (120), the guide may again be inserted through the sextant to define the axis of insertion for the second component (120). As with the first component (110), embodiments of the present disclosure may include positioning the trocar up against the bone to protect surrounding soft tissues (e.g., the skin or muscles) at the location where the pilot hole for the second component (120) is to be drilled. Using an appropriate surgical drill and corresponding drill bit, a pilot hole of appropriate diameter for receiving the second component (120) may then be drilled into and through the shaft of the femur in an upwardly direction, toward the pilot hole drilled for the first component (110). As stated above, some embodiments of the present disclosure may involve extending the pilot hole for the second component (120) up to and into the pilot hole for the first component (110). After debris is removed from the pilot hole, the second component (120) may be inserted.

When inserting the second component (120) into the pilot hole, the second component (120) may be pushed upwardly toward the first component (110) so as to engage the distal end (124) of the second component (120) with a portion of the first component (110) and provide an interlocking mechanical engagement between the two components (110,

120). Specific embodiments of such mechanical connections are discussed more fully below. In some embodiments of the present disclosure, the second component (120) may be inserted first, followed by insertion of the first component (110). In these embodiments, the second component (120) may have a through-hole provided in its distal end (124) through which the entire first component (110) may be inserted and maintained. The details of such embodiments are described in more detail below with respect to FIG. 8.

During implantation, the position of the patient may vary depending upon the type of fracture sought to be prevented or being treated. In the case of a pertrochanteric or subtrochanteric fracture, a traction table may be used with the patient lying on his or her back. This same positioning may also be used regardless of which side of the body the implant is being inserted into. In the case of a femoral neck fracture, the patient may be instructed to lay on his or her healthy side for preparation. When the implant is actually being inserted, a patient may be placed on his or her back, or on his or her side.

Figure 5A:
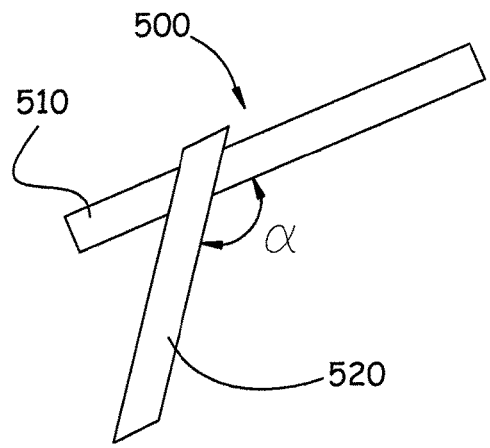
FIG. 5a shows an elevational view of an embodiment of an implant having a first component and second component, where the components are joined using a lateral plate and tabbed blade mechanical connection, according to some embodiments described herein.
Figure 5B:
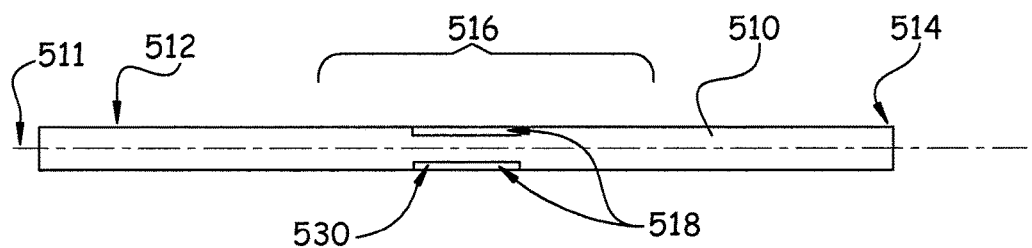

The mechanical connection between the two components may be accomplished using various different mechanisms. FIG. 5a shows an embodiment of an implant (500) according to the present disclosure, where a first component (510) and a second component (520) are connected using a plane and tabbed blade configuration. FIG. 5a shows the first component (510) and the second component (520) mechanically connected using this configuration, whereby the two components (510, 520) are mechanically engaged at an oblique angle, α, relative to one another. FIG. 5b more specifically shows a top plan view of an embodiment of the first component (510) having a longitudinal axis (511), proximal end (512), distal end (514) and middle portion (516). Some embodiments of the first component (510) may also have two or more lateral planes (530), as shown in FIG. 5b.

In some embodiments, the first component (510) may also be partially or fully cannulated and contain an inner lumen extending from the proximal end (512) to the distal end (514). The two or more lateral planes (530) may be formed in the first component (510) to provide for channels (518) using standard machining techniques. Each lateral plane (530) may be configured for mating contact with each face (552) of the blades (550). The lateral planes (530) may be located anywhere along the length of the first component (510). The embodiment depicted in FIG. 5a shows the lateral planes (530) being located in a middle portion (516) of the first component (510). The width of the lateral planes (530) and the depth of the channels (518) may be determined on a per-embodiment basis according to required design specifications, keeping in mind however that the structural integrity of the first component (510), as well as that of the overall implant (500), may be compromised as the width of the lateral plane and depth of the channels (518) increase. This is particularly true with regard to embodiments of the first component (510) that are partially or fully cannulated. In such embodiments, the channels (518) machined into the first component (510) may be as deep as necessary to provide the mechanical connection but not without compromising the overall strength or structural integrity of the implant.

Figure 5C:
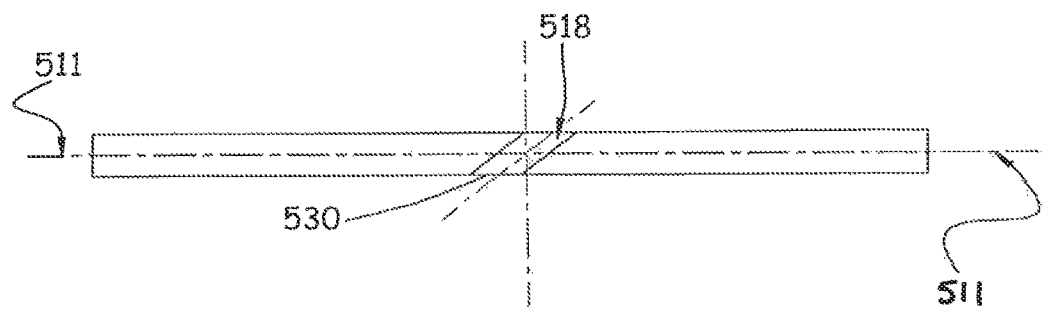

FIG. 5c shows an elevational view of the first component (510) shown in FIG. 5b. According to the embodiment depicted in FIG. 5c, the lateral planes (530) may be provided at an oblique angle relative to the longitudinal axis (511) of the first component (510). In some embodiments, this oblique angle will correspond to the oblique angle, α, at which the second component (520) is to be positioned relative to the first component (510).

Figure 5D:
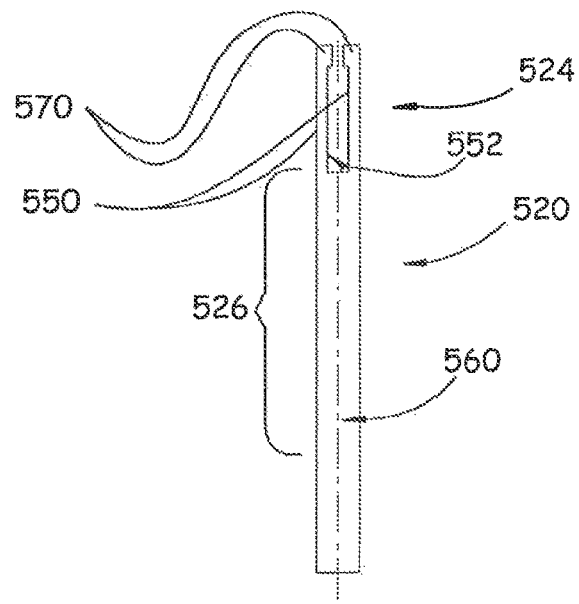

FIG. 5d shows an elevational view of an embodiment of the second component (520) having a longitudinal axis (521), proximal end (522), distal end (524) and middle portion (526). Some embodiments of the second component (520) may also have two or more blades (550) configured at the distal end (524), as shown in FIG. 5d. Each blade may have a face (552) for mating contact with each of the lateral planes (530). In some embodiments, the second component (520) may also be partially or fully cannulated and contain an inner lumen (560) for accommodating the injection of flowable material into the first component (510). The diameter of the inner lumen of the first component (510) may be sized as necessary to achieve the desired throughput of flowable material. The two or more blades (550) may be formed by being machined out of distal end (524) of the second component (520) or added onto the distal end (524) as a separate, pre-formed structure. In some embodiments, the blades (550) may contain tabs (570) positioned at the ends of the blades (550), as shown in FIG. 5d. Tabs (570) may function to retain the second component (520) in a locking relationship with the first component (510), according to some embodiments. The width of the blades (550) may vary depending on the embodiment, but should be sized no greater than the width of the lateral planes (530) so as to fit within the channels (518) and be in mating contact with the lateral planes (530). In some embodiments, the width of the blades (550) will be at least equal to the diameter of the second component (520) so as to provide a large surface area on the blades (550) for which to contact the lateral planes.

In operation, the mechanical connection between the first component (510) and the second component (520) to form the implant (500) may be established, according to some embodiments, by sliding the blades (550) of the second component (520) over the lateral planes (530) of the first component (510) until the tabs (570) pass by the lateral plane (530) and snap into place over top of the first component (510) so as to provide an interlocking mechanical connection between the two components (510, 520). When the two components (510, 520) are mechanically connected, the lateral planes (530) and the faces (552) of the blades (550) will be in contact with one another. In some embodiments, the width of the lateral planes (530) may be near-identical to the width of the blades (550) to provide a close, secure fit of the blades (550) within the channels (518) and against the lateral planes (530).

In some embodiments, appropriately dimensioned and positioned pilot holes for the first and second components (510, 520) will be provided in the bone in accordance with any known surgical procedure, including without limitation, those discussed above. The first component (510) may be inserted into its pilot hole to a depth such that the lateral planes (530) are linearly and rotationally aligned with the pilot hole of the second component. The second component (520) may be inserted upwardly into its pilot hole and toward the first component (510). The second component (520) is moved upwardly into its pilot hole until the tabs (570) pass over the lateral planes and snap into place over the top of the first component (510). Tabs (570) and a snug fit of the blades (550) within the channels (518) maintain the components (510, 520) in rigid interlocking engagement within the femur. The blades (550) should be designed to avoid breakage, have some degree of flexibility to withstand being expanded over the lateral planes (530) and maintain resilience to provide a locking engagement between the two components (510, 520). Regarding embodiments where the second component (520) is partially or fully cannulated, the thickness of the blades (550) may be approximately the thickness of the wall of the second component (520).

Figure 6A:
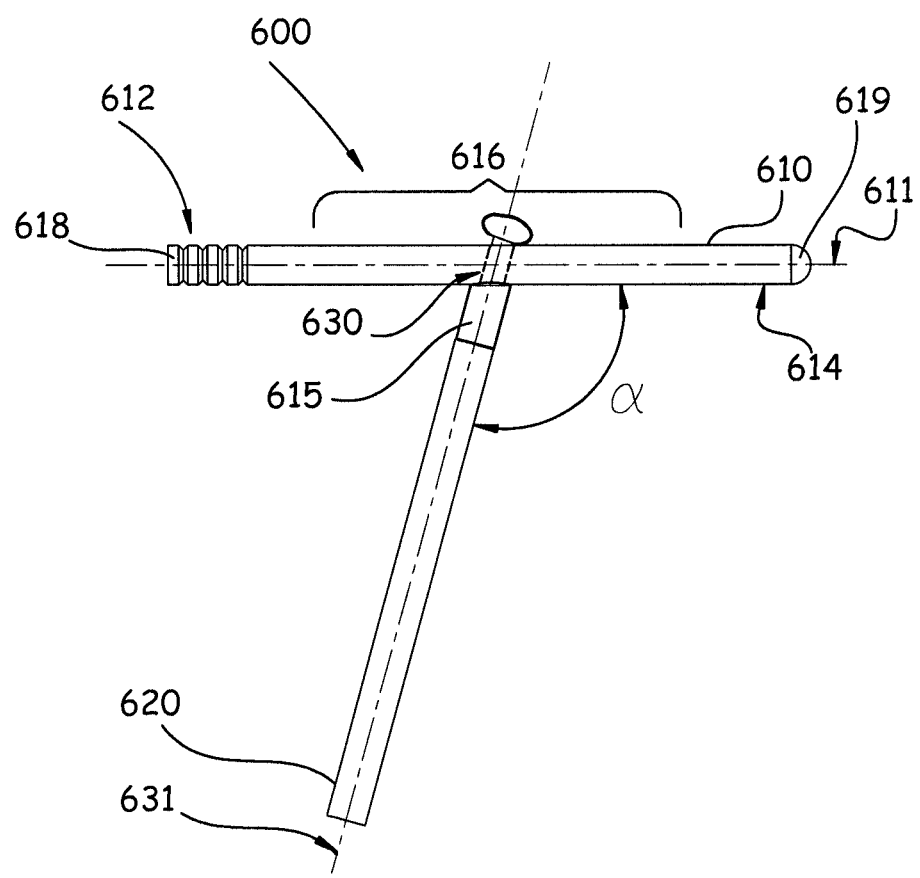
FIG. 6a shows an elevational view of an embodiment of an implant having a first component and a second component, where the components are joined using a through-hole and tabbed blade mechanical connection, according to some embodiments described herein.
Figure 6B:
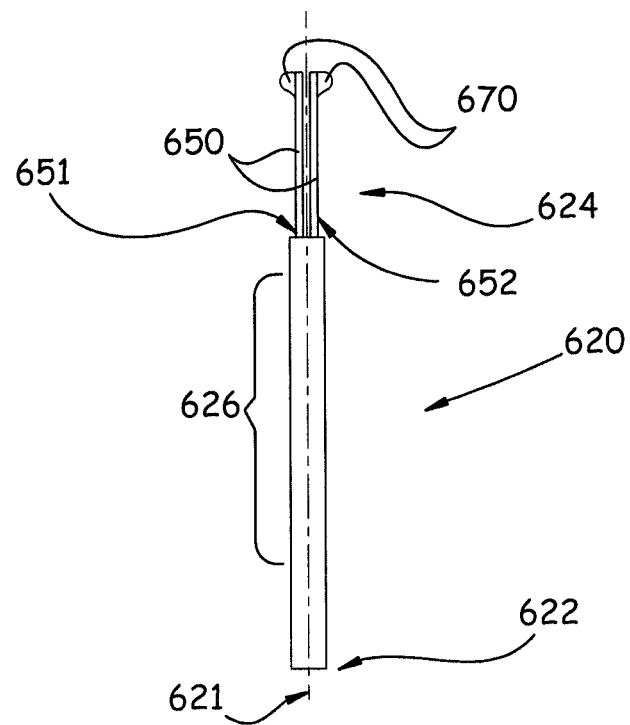

FIGS. 6a-6b show an embodiment of an implant (600) according to the present disclosure, where a first component (610) and a second component (620) are connected using a through-hole and tabbed blade configuration. FIG. 6a shows the first component (610) and the second component (620) mechanically connected using this configuration, whereby the two components (610, 620) are mechanically engaged at an oblique angle, α, relative to one another. FIG. 6a more specifically shows the first component (610) having a longitudinal axis (611), proximal end (612), distal end (614) and middle portion (616). Some embodiments of the first component (610) may also have a through-hole (630). The through-hole (630) may be circular, square, rectangular, oval, oblong, star-shaped or any other suitable shape. In some embodiments, the first component (610) may also be partially or fully cannulated and contain an inner lumen for accommodating the injection of flowable material into the first component (610). The diameter of the inner lumen of the first component (610) may be sized as necessary to achieve the desired throughput of flowable material. FIG. 6a specifically shows the first component (610) having peripheral grooves (618) and a rounded tip (619). While these features are shown here with regard to the implant (600), one or both of these features may be implemented on any embodiment of the present disclosure, e.g., implant (500), implant (700), implant (800) or implant (900) described herein.

In some embodiments, the through-hole (630) may be formed in the first component (610) as a round bore that extends entirely through diameter of the first component (610), using standard machining techniques. The through-hole (630) may be dimensioned appropriately so as to match the diameter of the second component (620), the collective width of the blades (650) of the second component (620) or otherwise snugly maintain the blades (650) in rigid, interlocking contact. The through-hole (630) may be located anywhere along the length of the first component (610). The embodiment depicted in FIG. 6a shows the through-hole (630) being located in a middle portion (616) of the first component (610). The diameter of the through-hole (630) should be determined on a per-embodiment basis according to required design specifications, keeping in mind that the structural integrity of the first component (610), as well as that of the overall implant (600), may be compromised as the diameter of the through-hole increases.

As shown in FIG. 6a, the through-hole (630) may be provided at an angle, such that longitudinal axis (631) of the through-hole (630) forms an oblique angle relative to the longitudinal axis (611) of the first component (610). In some embodiments, this oblique angle may correspond to the oblique angle, α, at which the second component (620) may be positioned relative to the first component (610). To accommodate the angle and guarantee a stable connection between the first component (610) and the second component (620), distal end (624) of second component (620), which is arranged to be within the through-hole (630) of the first component (610), may be truncated or otherwise formed in a wedge shape at an angle that corresponds to the oblique angle, α, so as to provide stable surface contact between the outside surface of the first component (610) and a face (651) of the second component (620).

Figure 6C:
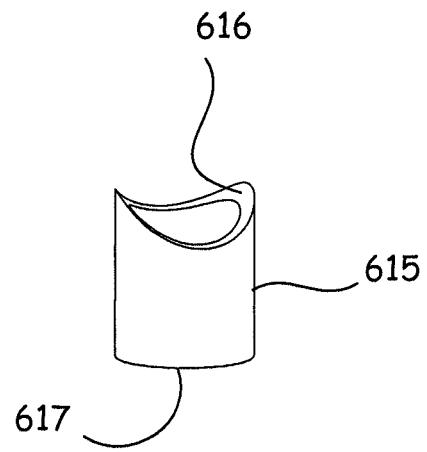
FIG. 6c shows a perspective view of a wedge component, according to some embodiments described herein.

Some embodiments may include a wedge (615) as a separate and additional component that may be positioned (e.g., placed, slipped and/or threaded) onto the second component (620), as shown in FIG. 6a. FIG. 6c shows an embodiment of the wedge (615) that is generally cylindrical with a diameter similar in size to that of the diameter of the second component (620). The wedge (615) may also contain an inner lumen portion to allow the wedge to be slipped over the one or more portions of the second component (620), including the two or more blades (650) discussed below. Embodiments of the wedge (615) may also be truncated at the angle corresponding to the oblique angle, α, between first component (610) and second component (620). A top surface (616) of the wedge 615 may also be concavely contoured so as to substantially match and receive in flush contact the convex outside surface of the first component (610). The wedge (615) may thus be configured to stabilize the first component (610) and second component (620) relative to each other by providing for flush surface contact between the wedge (615) and the outer surface of the first component (610). The wedge (615) may be of any suitable material, include polymer materials, metal, hard form and the like. In some embodiments, the wedge (615) may be positioned onto the second component (620) by sliding the wedge (615) over the two or more blades (650) at the distal end (624) and seating a bottom surface (617) of the wedge (615) against surface (651) of the second component (620). In other embodiments, the wedge (615) may be press fit onto the second component (620). While the wedge (615) is shown here with regard to the implant (600), the wedge (615) may be implemented on various embodiments of the present disclosure, e.g., implant (500), implant (700), implant (800) or implant (900), described herein.

FIG. 6b shows an elevation view of an embodiment of the second component (620) having a longitudinal axis (621), proximal end (622), distal end (624) and middle portion (626). Some embodiments of the second component (620) may also have two or more blades (650) configured at its distal end (624), as shown in FIG. 6b. Each blade (650) will have an outer face (652) for mating contact with the internal surfaces of the through-hole (630). To this end, the outer faces (652) may be shaped to correspond with the shape of the through-hole (630). For example, if the through-hole (630) is circular, the outer faces (652) of the blades (650) may have a corresponding convex shape to provide a snug, contacting fit with the through-hole (630). In some embodiments, the second component (620) may also be partially or fully cannulated and contain an inner lumen for accommodating the injection of flowable material into the first component (610). The diameter of the inner lumen of the first component (610) may be sized as necessary to achieve the desired throughput of flowable material. The blades (650) may be formed by being machined out of distal end (624) of the second component (620) or added onto the distal end (624) as a separate, pre-formed structure. In some embodiments, the blades (650) may contain tabs (670) positioned at the ends of the blades (650), as shown in FIG. 6b. Tabs (670) may function to retain the second component (620) in a locking relationship with the first component (610), according to some embodiments. The width of the blades (65(x)) may vary depending on the embodiment, but should be sized no greater than the diameter of the through-hole (630), so as to fit within the channels (618) and be in mating contact with the lateral planes (630). In some embodiments, the width of the blades (650) may be equal to the diameter of the second component (620) so as to provide a large surface area on the blades (650) for which to contact the lateral planes.

In operation, the mechanical connection between the first component (610) and the second component (620) to form the implant (600) may be established, according to some embodiments, by sliding the blades (650) of the second component (620) into and through the through-hole (630) of the first component (610) until the tabs (670) of the second component (620) pass through the through-hole (630) and snap into place on the outside of the through-hole (630) and against the outer surface of the first component (610) so as to provide an interlocking mechanical connection between the two components (610, 620). When the two components (610, 620) are mechanically connected, the internal surface of the through-hole (630) and outer faces (652) of the blades (650) will be in contact with one another. In some embodiments, the diameter of the through-hole (630) may be near-identical to the width of the blades (650) to provide a close, secure fit of the blades (650) within the through-hole (630).

In some embodiments, appropriately dimensioned and positioned pilot holes for the first and second components (610, 620) will be provided in the bone in accordance with any known surgical procedure, including without limitation, those discussed above. The first component (610) may be inserted into its pilot hole to a depth such that the through-hole (630) is linearly and rotationally aligned with the pilot hole of the second component (620). The second component (620) may be inserted upwardly into its pilot hole and toward the first component (610). The second component (620) may be moved upwardly into its pilot hole until the tabs (670) pass through the through-hole (630) and snap into place on the outer surface of the first component (610). Tabs (670) and a snug fit of the blades (650) within the through-hole (630) maintain the components (610, 620) in rigid interlocking engagement within the femur. The blades (650) should be designed to avoid breakage, have some degree of flexibility to withstand being compressed within the through-hole (630) during insertion and maintain resilience to provide a locking engagement between the two components (610, 620). Regarding embodiments where the second component (620) is partially or fully cannulated, the thickness of the blades (650) may be approximately the thickness of the wall of the second component (620).

Figure 7A:
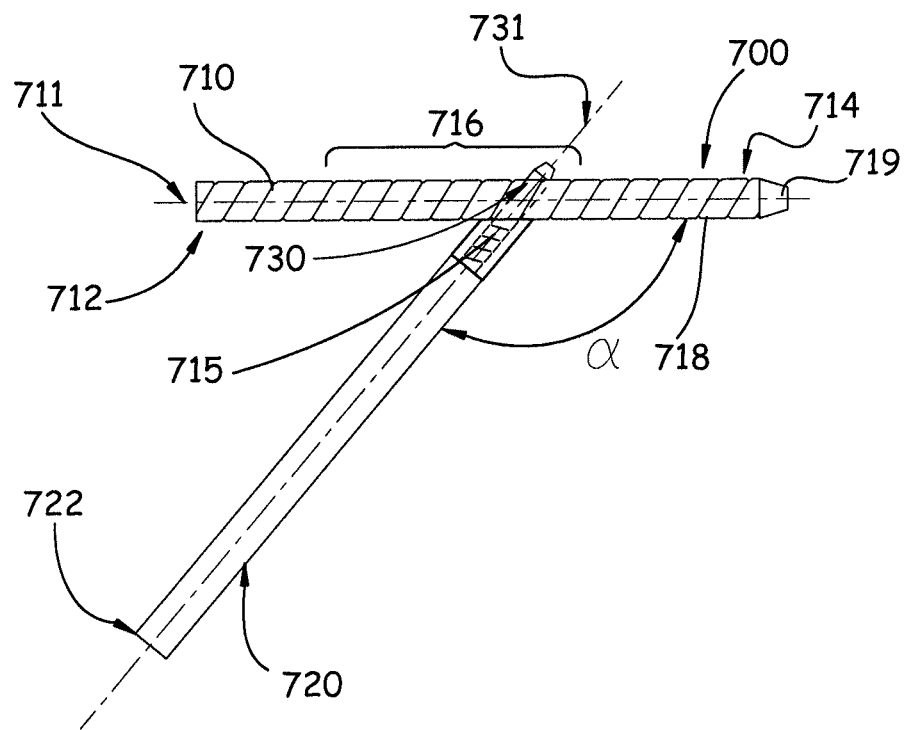
FIG. 7a shows an elevational view of an embodiment of an implant having a first component and a second component, where the components are joined using a threaded hole and threaded tip mechanical connection, according to some embodiments described herein.
Figure 7B:
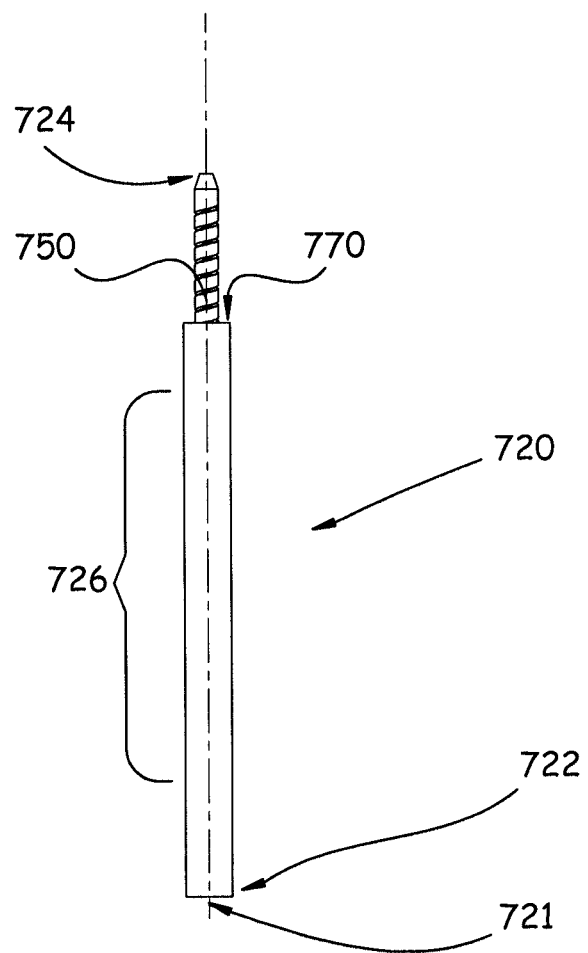

FIGS. 7a-7b show an embodiment of an implant (700) according to the present disclosure, where a first component (710) and a second component (720) are connected using a threaded hole and threaded tip configuration. FIG. 7a shows the first component (710) and the second component (720) mechanically connected using this configuration, whereby the two components (710, 720) are mechanically engaged at an oblique angle, α relative to one another. The first component (710) having a longitudinal axis (711), proximal end (712), distal end (714) and middle portion (716). Some embodiments of the first component (710) may also have a threaded hole (730), as shown in FIG. 7a. The threaded hole (730) must be circular to accommodate a threaded connection with the second component (720). The threaded hole (730) may be formed by standard machining techniques. The size of the threaded hole (730) and the choice of thread type will depend on the design requirements but, in any event, should correspond to the size and thread type of the threaded tip (750) of the second component (720).

In some embodiments, the first component (710) may also be partially or fully cannulated and contain an inner lumen extending from the proximal end (712) to the distal end (714). FIG. 7a specifically shows the first component (710) having threads (718) and a chamfered tip (719). While these features are shown here with regard to the implant (700), one or both of these features may be implemented on various embodiments of the present disclosure, e.g., implant (500), implant (600) or implant (800), described herein. In some embodiments, the threaded hole (730) may be formed in the first component (710) to extend entirely through the first component (710). The threaded hole (730) may be located anywhere along the length of the first component (710). The embodiment depicted in FIG. 7a shows the threaded hole (730) being located in a middle portion (716) of the first component (710). The size and thread type of the threaded hole (730) and corresponding threaded tip (750) may be determined on a per-embodiment basis according to required design specifications, keeping in mind that the structural integrity of the first component (710), as well as that of the overall implant (700), may be compromised as the size of the threaded hole (730) increases.

As shown in FIG. 7a, the threaded hole (730) may be provided at an angle, such that longitudinal axis (731) of the threaded hole (730) forms an oblique angle relative to the longitudinal axis (711) of the first component (710). In some embodiments, this oblique angle may correspond to the oblique angle, .alpha., at which the second component (720) is to be positioned relative to the first component (710). To accommodate the angle and guarantee a stable connection between the first component (710) and the second component (720), distal end (724) of second component (720), which is arranged to be within the threaded hole (730) of the first component (710), may be truncated or otherwise formed in a wedge shape at an angle that corresponds to the oblique angle, .alpha., so as to provide stable surface contact between the outside surface of the first component (710) and a distal face (770) of the second component (720). Furthermore, as explained with respect to implant (600), some embodiments may include a separate component, e.g., wedge (715), positioned on (e.g., placed, slipped and/or threaded) onto the second component (720), as shown in FIG. 7a.

FIG. 7b shows an elevational view of an embodiment of the second component (720) having a longitudinal axis (721), proximal end (722), distal end (724) and middle portion (726). Some embodiments of the second component (720) may have a threaded tip (750) configured at its distal end (724), as shown in FIG. 7b. The threaded tip (750) may be formed by machining the end of the second component (720) or may be a separate, pre-formed structure added to the distal end (724) of the second component (720). The threaded tip (750) may be any suitable size, with any suitable thread type, as long as the threaded tip (750) design specifications correspond with those of the threaded hole (730) of the first component (710) to provide a secure mechanical connection between the two components (710, 720). In some embodiments, the second component (720) may also be partially or fully cannulated and contain an inner lumen for accommodating the injection of flowable material into the first component (710). The diameter of the inner lumen of the first component (710) may be sized as necessary to achieve the desired throughput of flowable material. When the second component (720) is cannulated, the threaded tip (750) may also be partially or fully cannulated, according to some embodiments. In some embodiments, the threaded tip (750) may be solid.

In operation, the mechanical connection between the first component (710) and the second component (720) to form the implant (700) may be established, according to some embodiments, by threading the threaded tip (750) of the second component (720) into the threaded hole (730) of the first component (710) until the distal face (770) of the second component (720), shown in FIG. 7b, comes into contact with the first component (720). Sufficient tightening of the distal face (770) against the outer surface of the first component (710) provides an interlocking mechanical connection between the two components (710, 720). To enable such tightening, the second component (720) may have an engaging portion (not shown) located at its proximal end (722). The engaging portion may be configured to receive a slotted screwdriver, a Phillips head screwdriver, hex key or any other suitable tightening tool.

In some embodiments, appropriately dimensioned and positioned pilot holes for the first and second components (710, 720) will be provided in the bone in accordance with any known surgical procedure, including without limitation, those discussed above. The first component (710) may be inserted into its pilot hole to a depth such that the threaded hole (730) is linearly and rotationally aligned with the pilot hole of the second component (720). Next, the second component (720) may be inserted upwardly into its pilot hole toward the pilot hole of the first component (710). The second component (720) is moved upwardly into its pilot hole until the threaded tip (750) reaches the threaded hole (730). At this point, the second component (720) may be rotated to thread the threaded tip (750) into the threaded hole (730) until the distal face (770) contacts the outer surface of the first component (710). The threaded tip (750) should be dimensioned and made of a material sufficient to avoid breakage and withstand mechanical stresses imposed upon the implant (700), such as tension or torsion occurring within the hip joint due to movement.

Figure 8:
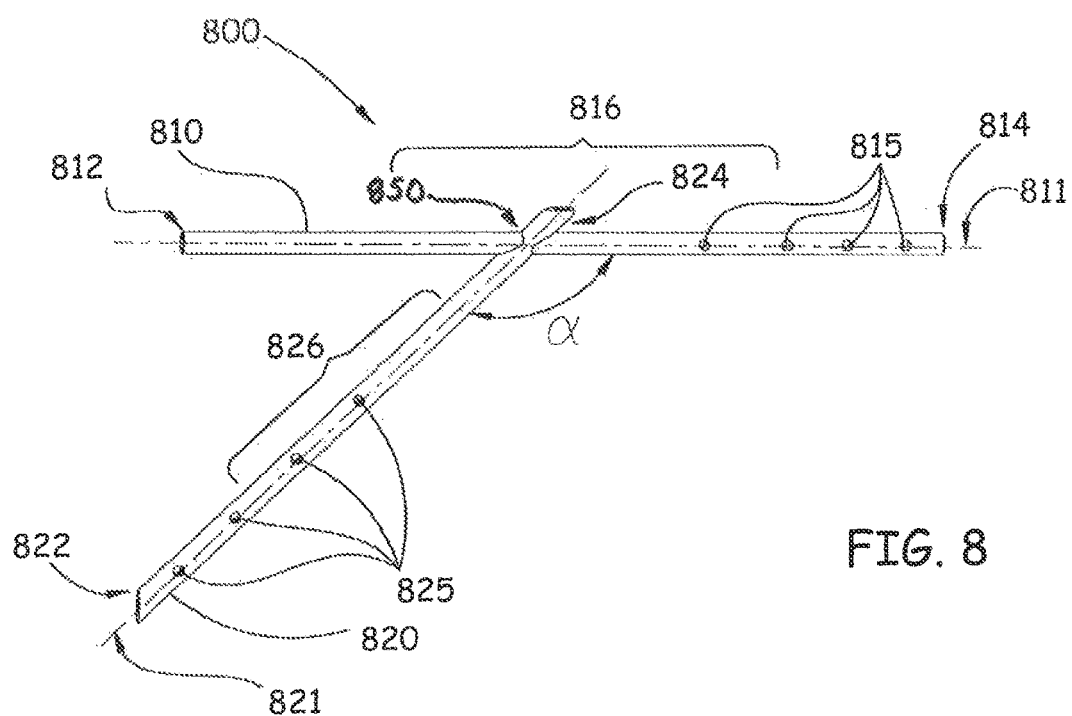
FIG. 8 shows a perspective view of an embodiment of an implant having a first component and a second component, where the components are joined using a sliding fit of one component within a through-hole contained in the other component, according to some embodiments described herein.

FIG. 8 shows an embodiment of an implant (800) according to the present disclosure, where a first component (810) and a second component (820) are connected in a sliding engagement configuration. FIG. 8 shows the first component (810) and the second component (820) mechanically connected using this configuration, whereby the two components (810, 820) are mechanically engaged at an oblique angle, α, relative to one another. The first component (810) may have a longitudinal axis (811), proximal end (812), distal end (814) and middle portion (816). In some embodiments, the first component (810) may be configured as a cylindrical rod having a plurality of holes (815) positioned longitudinally and/or peripherally along the first component (810). While FIG. 8 depicts the holes (815) as circular and of a specific, uniform size, each hole (815) may be of any shape (e.g., oval, oblong, triangular, square, rectangular, star-shaped or diamond) or dimension in accordance with design requirements and desired functionality. The holes (815) may be formed by drilling or any other standard machining process. According to some embodiments, the first component (810) may also be partially or fully cannulated along its entire longitudinal axis (811) and contain an inner lumen (not shown) for accommodating the injection of flowable material into the first component (810) and through the holes (815) into surrounding cancellous bone. The diameter of the inner lumen of the first component (810) may be sized as necessary to achieve the desired throughput of flowable material. Furthermore, the outer diameter of the first component (810) may be any suitable dimension, as long as it is sized appropriately so as to fit within the through-hole (850) in the distal end (824) of the second component (820).

In some embodiments, the second component (820) may also be configured as a cylindrical rod having a plurality of holes (825) positioned longitudinally and/or peripherally along a middle portion (826) of the second component (820), as shown in FIG. 8. As with the holes (815) of the first component (810), the holes (825) of the second component (820) may also be circular and of a specific, uniform size, as depicted in FIG. 8. However, each hole (825) may be of any shape (e.g., oval, oblong, triangular, square, rectangular, star-shaped or diamond) or dimension in accordance with design requirements and desired functionality. The holes (825) may also be formed by drilling or other standard machining process. In some embodiments, the second component (820) may also be partially or fully cannulated along its entire longitudinal axis (821) and contain an inner lumen (not shown) for accommodating the injection of flowable material into the second component (820) and through the holes (825) into surrounding cancellous bone. The diameter of the inner lumen of the second component (820) may be sized as necessary to achieve the desired throughput of flowable material.

In some embodiments, the second component (820) may also have a through-hole (850) formed in its distal end (824) for receiving the first component (810), as shown in FIG. 8. The through-hole (850) may be formed by machining a hole through the distal end (824) of the second component (820). The diameter of the through-hole (850) should be sized appropriately so as to accommodate the outer diameter of the first component (810). In some embodiments, the difference between the diameter of the through-hole (850) and the outer diameter of the first component (810) may be minimal so as to provide a close fit that securely engages the first component (810) within the second component (820), yet allows the first component (810) to slide within and relative to the second component (820) when sufficient force is applied. The through-hole (850) may be sized as necessary to provide for an interlocking mechanical engagement between the two components (810, 820), but without compromising the structural integrity of the second component (820), as well as the implant (800) as a whole.

According to some embodiments, the through-hole (850) may be provided at an angle, such that the longitudinal axis (811) of the first component (810) forms an oblique angle relative to the longitudinal axis (821) of the second component (820) when the two components are mechanically connected. In some embodiments, this oblique angle may correspond to the oblique angle, α, at which the second component (820) is to be positioned relative to the first component (810).

In operation, the mechanical connection between the first component (810) and the second component (820) to form the implant (800) may be established, according to some embodiments, by sliding the first component (810) into the through-hole (850) of the second component (820). While FIG. 8 shows the first component (810) being engaged with the through-hole (850) along its middle portion (816), the first component (810) may alternatively be engaged with the through-hole (850) more toward its distal end (814) or its proximal end (812).

In some embodiments, appropriately dimensioned and positioned pilot holes for the first and second components (810, 820) will be provided in the bone in accordance with any known surgical procedure, including without limitation, those discussed above. The implant (800) may be formed by inserting the second component (820) into its pilot hole to a depth such that the distal end (824) containing the through-hole (850) extends into the pilot hole created for the first component (810). When inserting the second component (820), the second component (820) may be rotationally aligned within its pilot hole such that the through-hole (850) is in a position to receive the first component (810). In other words, the longitudinal axis (not shown) of the through-hole (850) is substantially aligned with the longitudinal axis (not shown) of the pilot hole for the first component (810). The first component (810) may be inserted into its pilot hole and into and through the through-hole (850) until the distal end (814) reaches the bottom of the pilot hole of the first component (810). The engagement between the first component (810) and the through-hole (850) of the second component (820), as well as any anchorage provided by flowable material injected into either or both components (810, 820) and/or any textures or chemical treatments on the outer surface of one or both of the components, will maintain the mechanical connection between the components to securely hold the implant (800) within the bone.

Figure 9:
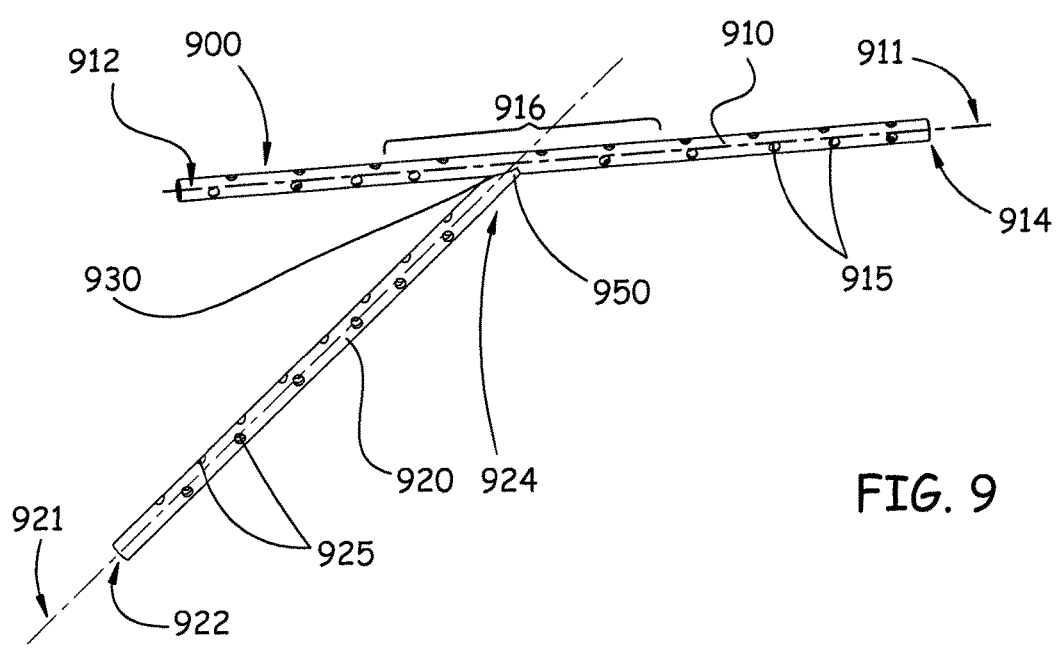
FIG. 9 shows a perspective view of an embodiment of an implant having a first component and second component, where the second component is partially inserted into the first component, according to some embodiments described herein.

FIG. 9 shows another embodiment of an implant (900) having a first component (910) and a second component (920) according to the present disclosure, where the first component (910) and the second component (920) are mechanically connected by partially inserting a machined tip (950) located at the distal end (924) of the second component (920) into an opening (930) provided in the first component (910). As with the embodiments discussed above, the two components (910, 920) may be mechanically engaged at an oblique angle, α, relative to one another. The first component (910) may have a longitudinal axis (911), proximal end (912), distal end (914) and middle portion (916). The first component (910) may also have the opening (930) for receiving the machined tip (950) located at the distal end (924) of the second component (920). The opening (930) may be dimensioned with a depth and width (e.g., a diameter) sufficient to maintain the machined tip (950) of the second component (920) in interlocked engagement.

In some embodiments, the first component (910) may be configured as a cylindrical rod having a plurality of holes (915) positioned longitudinally and/or peripherally along the first component (910). While FIG. 9 depicts the holes (915) as circular and of a specific, uniform size, each hole (915) may be of any shape (e.g., oval, oblong, triangular, square, rectangular, star-shaped or diamond) or dimension in accordance with design requirements and desired functionality. The holes (915) may be formed by drilling or any other standard machining process. According to some embodiments, the first component (910) may also be partially or fully cannulated along its entire longitudinal axis (911) and contain an inner lumen (not shown) for accommodating the injection of flowable material into the first component (910) and through the holes (915) into surrounding cancellous bone. The diameter of the inner lumen of the first component (910) may be sized as necessary to achieve the desired throughput of flowable material. Furthermore, the outer diameter of the first component (910) may be any suitable dimension, as long as it is sized appropriately so as to provide for engagement with the machined tip (950) of the second component (920).

In some embodiments, the second component (920) may also be configured as a cylindrical rod having a plurality of holes (925) positioned longitudinally and/or peripherally along the second component (920). As with the holes (915) of the first component (910), the holes (925) of the second component (920) may also be circular and of a specific, uniform size. However, each hole (925) may be of any shape (e.g., oval, oblong, triangular, square, rectangular, star-shaped or diamond) or dimension in accordance with design requirements and desired functionality. The holes (925) may also be formed by drilling or other standard machining process. In some embodiments, the second component (920) may also be partially or fully cannulated along its entire longitudinal axis (921) and contain an inner lumen (not shown) for accommodating the injection of flowable material into the second component (920) and through the holes (925) into surrounding cancellous bone. The diameter of the inner lumen of the second component (920) may be sized as necessary to achieve the desired throughput of flowable material.

In some embodiments, the second component (920) may have the machined tip (950) formed at its distal end (924) for mechanical connection with the opening (930) of the first component (910), as shown in FIG. 9. The machined tip (950) may be firmed in the distal end (924) by standard machining techniques and may be threaded for threadable engagement with the opening (930), tabbed for locked engagement with the opening (930) or tapered with a plurality of diameters to provide a press fit within the opening (930). Thus, in some embodiments, the dimensions of the opening (930) should be sized appropriately so as to accommodate the machined tip (950) in interlocking engagement. In some embodiments, the difference between the dimensions of the machined tip (950) and those of the opening (930) may be minimal so as to provide a close fit that securely engages the second component (920) within the first component (910). The opening (930) may be sized as necessary to provide for an interlocking mechanical engagement between the two components (910, 920), but without compromising the structural integrity of the first component (910), as well as the implant (900) as a whole.

According to some embodiments, the opening (930) and the machined tip (950) may be configured such that the longitudinal axis (911) of the first component (910) forms an oblique angle relative to the longitudinal axis (921) of the second component (920) when the two components are mechanically connected. In some embodiments, this oblique angle will correspond to the oblique angle, α, at which the second component (920) is to be positioned relative to the first component (910). In operation, the mechanical connection between the first component (910) and the second component (920) to form the implant (900) may be established, according to some embodiments, by threading, sliding, pushing, and/or pressing the machined tip (950) of the second component (920) into the opening (930) of the first component (910). While FIG. 9 shows the second component (910) being engaged along the middle portion (916) of the first component (910), the second component (920) may also be engaged more toward the distal end (914) of the first component (910).

FIG. 10 shows an embodiment of a component (1000) (i.e., either or both of the first component (110) and/or second component (120)) comprising a two-part configuration that provides for adjusting the length of the component (1000), according to the present disclosure. The component (1000) may include a tube (1010) having a proximal end (1012), a distal end (1014) and internal threads (1018) and a rod (1020) having a proximal end (1022), a distal end (1024) and external threads (1028). In some embodiments, the internal threads (1018) may begin at either the proximal end (1012), the distal end (1014) or therebetween and traverse the entire length of the tube (1010) or only a portion of the length of the tube (1010). In some embodiments, the external threads (1028) may begin at the distal end (1024) of the rod (1020) and traverse the entire length of the rod (1020) or only a portion of the length of the rod (1020). In some embodiments, the rod (1028) may also be partially or fully cannulated and contain an inner lumen (1060) for accommodating the injection of flowable material into the rod (1020). The diameter of the inner lumen of the rod (1020) may be sized as necessary to achieve the desired throughput of flowable material. In some embodiments that are fully or partially cannulated, the walls of the tube (1010) and/or rod (1020) may have one or more holes (not shown)

for diffusing flowable material from the inner lumen of the tube (1010) and/or rod (1020) into the surrounding cancellous bone. The holes may be circular, oval, oblong, square or any other suitable shape. The holes also may be positioned longitudinally or peripherally along the component.

In operation, some embodiments may involve inserting the component (1000) into a corresponding pilot hole in an assembled state and thereafter adjusting the length thereof by threading or unthreading one part relative to the other part by rotating motion. The distal end (1014) of the tube (1010) or the proximal end (1022) of the rod (1020), as depicted in FIG. 10, may be configured with an engaging portion to receive a slotted screwdriver, a Phillips head screwdriver, hex key or any other suitable tightening tool to enable such rotation motion. In some embodiments, either the tube (1010) or the rod (1020) of the two-part configuration (1000) may be inserted first into a corresponding pilot hole with the remaining component inserted into the pilot hole for threaded engagement with the already-inserted component. In some embodiments, the tube (1010) may be inserted into the pilot hole first and the rod (1020) is thereafter threaded into the tube (1010) by rotating the rod (1020) until the rod (1020) has reached the desired depth within the tube (1020) and/or into the pilot hole. In some embodiments, the rod (1020) may be inserted into the pilot hole first and the tube (1010) is thereafter threaded onto the rod (1010) by rotating the tube (1010) until the tube has reached the desire distance onto the rod (1010) and/or into the pilot hole. The tube (1010) and/or rod (1020) may be configured with any of the features discussed herein with respect FIGS. 4-9.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with the following claims and their equivalents.

What is claimed is:

1. A medical device for remedying and/or preventing fractures in the hip-joint, the hip-joint including a femur having outer cortical bone and inner cancellous bone and comprising a long bone, a femoral head, and a femoral neck having a longitudinal axis (FNLA) intersecting with the a long axis of the long bone, the device comprising:
    a first hollow tubular implant having a proximal end, a distal end, a middle portion, a smooth outer surface, and a first implant longitudinal axis (FCLA), the first implant being configured for implantation within the femoral neck of the femur such that the FCLA aligns with the FNLA, the smooth outer surface configured to facilitate insertion of the first implant into the femoral neck when the first implant is pushed into the femoral neck; and
    a second hollow tubular implant having a proximal end, a distal end, a middle portion, an outer surface, and a second implant longitudinal axis (SCLA), the second implant being configured for implantation within the long bone of the femur;
    wherein the device is configured such that upon implantation:
        the distal end of the second implant interlocks with the middle portion or the distal end of the first implant at a connection point,
        the second implant is oriented at an oblique angle relative to the first component such that the proximal end of the second implant intersects with cortical bone at a proximal end of the long bone of the femur; and
        the proximal ends of the first implant and the second implant protrude from the surface of cortical bone, such that the protruding proximal end of the second implant is situated at a distance further from the hip joint than the protruding proximal end of the first implant.

2. The device of claim 1, wherein the device is additionally configured such that upon implantation, the proximal end of the second implant is positioned at a distance further from the femoral head than that the proximal end of the first implant.

3. The device of claim 1, wherein the first implant includes a first opening arranged on the middle portion or distal end thereof, the first opening for receiving the distal end of the second implant and interlocking therewith.

4. The device of claim 3, wherein the first opening comprises a through-hole traversing the first implant, the first opening having a proximal side arranged to receive the distal end of the second implant, and a distal side opposite the proximal side.

5. The device of claim 4, wherein the distal end of the second implant includes a plurality of tabbed blades configured to engage with the first opening of the first implant such that the tabbed blades traverse the center of the through-hole and engage with the distal side of the through-hole so as to interlock the second implant therewith.

6. The device of claim 1, wherein the oblique angle has a value within the range of 91 degrees to 179 degrees.

7. The device of claim 1, wherein the outer surface of the second implant further comprises a knurled surface.

8. The device of claim 1, wherein the outer surface of the second implant further comprises a bioactive coating.

9. The device of claim 1, wherein a portion of the first implant has a generally cylindrical shape, and another portion of the first implant has a shape selected from the group of shapes consisting of oval, star, diamond, square and rectangular.

10. The device of claim 1, wherein the outer surface of the second implant further comprises longitudinal grooves.

11. The device of claim 1, wherein the outer surface of the second implant further comprises circumferential grooves allowing for the second implant to be cut and adjusted in length.

12. The implant of claim 1, wherein:
    the FCLA forms a first angle with the long axis of the long bone,
    the SCLA forms a second angle with the long axis of the long bone, and
    wherein the second angle is greater than the first angle.

13. The device of claim 1, wherein the distal end of the second implant interlocks with the middle portion or distal end of the first implant via threaded engagement.

14. The device of claim 1, wherein at least one of the implants comprises at least one opening at the respective proximal end thereof configured for injecting a composition of a biocompatible bone cement upon implantation of the device.

15. The device of claim 1, wherein the outer surface of at least one of the implants includes a surface treatment to enhance biocompatibility and development of cell tissues.

* * * * *